(12) United States Patent
Raison

(10) Patent No.: US 9,579,044 B2
(45) Date of Patent: Feb. 28, 2017

(54) METHOD AND SYSTEM FOR DECOMPOSING SUPERIMPOSED GROUND REACTION FORCES INTO INDIVIDUAL FORCE PROFILES

(71) Applicant: POLYVALOR, LIMITED PARTNERSHIP, Montreal (CA)

(72) Inventor: Maxime Raison, Montreal (CA)

(73) Assignee: POLYVALOR, LIMITED PARTNERSHIP, Montréal, Quebec (CA)

( * ) Notice: Subject to any disclaimer, the term of this patent is extended or adjusted under 35 U.S.C. 154(b) by 0 days.

(21) Appl. No.: 14/780,426

(22) PCT Filed: Mar. 28, 2014

(86) PCT No.: PCT/CA2014/000302
§ 371 (c)(1),
(2) Date: Sep. 25, 2015

(87) PCT Pub. No.: WO2014/153650
PCT Pub. Date: Oct. 2, 2014

(65) Prior Publication Data
US 2016/0045139 A1    Feb. 18, 2016

Related U.S. Application Data

(60) Provisional application No. 61/805,984, filed on Mar. 28, 2013.

(51) Int. Cl.
*G01L 1/00* (2006.01)
*A61B 5/103* (2006.01)
(Continued)

(52) U.S. Cl.
CPC .............. *A61B 5/1038* (2013.01); *G01L 5/16* (2013.01); *G06K 9/00348* (2013.01); *G06K 9/00496* (2013.01)

(58) Field of Classification Search
CPC .. A61B 5/1038; G06K 9/00348; G01L 5/225; G01L 5/16
(Continued)

(56) References Cited

U.S. PATENT DOCUMENTS 5,772,522 A * 6/1998 Nesbit ............... A63B 24/0003
434/252
7,552,021 B2    6/2009 Bar-Haim et al.
(Continued)

OTHER PUBLICATIONS

International Search Report and Written Opinion for Int. App. No. PCT/CA2014/000302, mailed Jul. 8, 2014.
(Continued)

*Primary Examiner* — Max Noori
(74) *Attorney, Agent, or Firm* — McDonnell Boehnen Hulbert & Berghoff LLP

(57) ABSTRACT

A method for decomposing a GRF into individual force profiles, comprising: receiving a global GRF measured while a subject performs at least one movement on the force platform, the movement comprising at least two motion configurations; identifying individual time regions contained in the time measurement of the global GRF and assigning a respective one of the at least two motion configurations to each time region using a logical order of motion configurations and an identification of a reference motion configuration; for each time region, determining an individual GRF for each one of the at least two support contacts using the identification of the motion configuration for the time region and the global GRF, thereby determining a contribution of each one of the at least two support contacts to the global GRF; and outputting the individual GRFs.

17 Claims, 7 Drawing Sheets

(51) Int. Cl.
G06K 9/00 (2006.01)
G01L 5/16 (2006.01)

(58) Field of Classification Search
USPC .............................. 73/818, 862.381, 862.391
See application file for complete search history.

(56) References Cited

U.S. PATENT DOCUMENTS

| | | | | |
|---|---|---|---|---|
| 2004/0199089 | A1* | 10/2004 | Tasch | A01K 29/00 600/587 |
| 2011/0231050 | A1* | 9/2011 | Goulding | B62D 57/024 701/26 |
| 2013/0204545 | A1* | 8/2013 | Solinsky | G01P 13/00 702/44 |
| 2014/0148265 | A1* | 5/2014 | Kim | G06K 9/00342 473/269 |

OTHER PUBLICATIONS

Ballaz, L., et al., "Decomposition of the vertical ground reaction forces during gait on a single force plate," J Musculoskelet Neuronal Interact, vol. 13, No. 2, pp. 236-243, Jun. 2013.
Chumanov, E. S., et al., "Computational techniques for using insole pressure sensors to analyse three-dimensional joint kinetics," Computer Methods in biomechanics and Biomedical Engineering, vol. 13, Iss. 3, pp. 1-10, Jun. 2010.
Kimura, A., et al., "The method for separation of superimposed ground reaction forces and center of pressures of gait during double stance phase," International Society of Biomechanics, Ninth International Symposium on the 3D Analysis of Human Movement, Jun. 2006.
Masani, K., et al., "Variability of ground reaction forces during treadmill walking," J Appl Physiol, vol. 92, pp. 1885-1890, Jan. 2002.
Oh, S. E., et al., "Prediction of ground reaction forces during gait based on kinematics and a neural network model," Journal of Biomechanics, vol. 46, Issue 14, pp. 2372-2380, Sep. 2013.
Raison, M., et al., "Determination of ground reaction forces and centers of pressure of both feet during normal walking n a single platform," Computer Methods in Biomechanics and Biomedical Engineering, Supplement 1, pp. 227-228, 2005.
Begg, R. K., et al., "A Method for the Reconstruction of Ground Reaction Force-Time Characteristics During Gait from Force Platform Recordings of Simultaneous Foot Falls," IEEE Transactions on Biomedical Engineering, vol. 47, No. 4, pp. 547-551, Apr. 2000.
Davis, B. L., et al., "Decomposition of Superimposed Ground Reaction Forces Into LEft and Right Force Profiles," J. Biomechanics, vol. 26. No. 4/5. pp. 593-597, 1993.
Dierick, F., et al., "A force measuring treadmill in clinical gait analysis," Gait and Posture, vol. 20, pp. 299-303, 2004.
Dingwell, J.B., et al., "Use of an instrumented treadmill for real-time gait symmetry evaluation and feedback in normal and transtibial amputee subjects," Prosthetics and Orthotics International, vol. 20, pp. 101-110, 1996.
Gottschall, J.S., et al., "Energy cost and muscular activity required for propulsion during walking," J Appl Physiol, vol. 94, pp. 1766-1772, 2003.
Grabowski, A.M., "Metabolic and Biomechanical Effects of Velocity and Weight Support Using a Lower-Body Positive Pressure Device During Walking," Arch Phys Med Rehabil, vol. 91, pp. 951-957, Jun. 2010.
Janssen, D., et al., "Diagnosing fatigue in gait patterns by support vector machines and self-organizing maps," Human Movement Science, vol. 30, pp. 966-975, 2011.
Kram, R., et al., "Force treadmill for measuring vertical and horizontal ground reaction forces," J Appl Physiol, vol. 85 No. 2, pp. 764-769, 1998.
Kurz, M.J., et al., "Differences in the dynamic gait stability of children with cerebral palsy and typically developing children," Gait & Posture, vol. 36, pp. 600-604, 2012.
Martin, P.E., et al., "Step length and frequency effects on ground reaction forces during walking," Journal of Biomechanics, vol. 25, No. 10, pp. 1237-1239, 1992.
Oggero, E., et al., "Probability of Valid Gait Data Acquisition Using Currently Available Force Plates," Biomedical Sciences Instrumentation, vol. 34, pp. 392-397, 1998.
Roerdink, M., et al., "Online gait event detection using a large force platform embedded in a treadmill," Journal of Biomechanics, vol. 41, pp. 2628-2632, 2008.
Stolze, H., et al., "Retest reliability of spatiotemporal gait parameters in children and adults," Gait and Posture, vol. 7, pp. 125-130, 1998.
Sutherland, D.H., et al., "The Development of Mature Gait," Journal of Bone and Joint Surgery, p. 336, 1990.
Veilleux, L-N., et al., "Gait analysis using a force-measuring gangway: Intrasession repeatability in healthy adults," J Musculoskelet Neuronal Interact, vol. 11, No. 1, pp. 27-33, 2011.

* cited by examiner

METHOD AND SYSTEM FOR DECOMPOSING SUPERIMPOSED GROUND REACTION FORCES INTO INDIVIDUAL FORCE PROFILES

CROSS-REFERENCE TO RELATED APPLICATIONS

The present application is a U.S. National Phase Application pursuant to 35 U.S.C. §371 of International Application No. PCT/CA2014/000302, filed Mar 28, 2014, which claims priority of U.S. Provisional Patent Application No. 61/805,984, filed on Mar. 28, 2013. The entire disclosure contents of these applications are herewith incorporated by reference into the present application.

TECHNICAL FIELD

The present invention relates to the field of method and system for analyzing the gait of a subject, and particularly decomposing a group reaction force into individual force profiles.

BACKGROUND

In gait laboratory, ground reaction forces (GRFs) are recorded using floor-mounted force platforms in order to evaluate GRF patterns and compute the joint torques using either an inverse dynamic approach or an angular momentum calculus, as known in the art. Traditionally, to obtain valid measurement a subject must place two consecutive steps on individual force platforms with no foot contact outside the surface of the individual force platforms (usually 50×50 cm). This condition can lead to an important number of trials before achieving valid measurements because the subject must not voluntarily "target" the force platforms with their footsteps. In fact, in target conditions, the participant is prone to change his/her gait pattern, which could impact GRF measurements. A change in step length, as little as substantially 10%, has been shown to affect GRFs. Thereby, targeting has been cited as a major limitation of gait studies.

Gait studies have intuitively attempted to reduce the effect of targeting, and simultaneously reduce the number of redundant trials, by fine-tuning each subject starting position in order to make the footsteps coincide with the force platforms. Nevertheless, the number of trials made to obtain valid GRF measurements could remain important because starting position definition is especially uncertain with people with impaired gait, as well as in children, because of the spatiotemporal gait parameters variability. Thereby, recording several trials across the force platforms, until a series of adequate tests have been performed, impose a lot of trials and can be time consuming. The duration of gait evaluation may be problematic in children because their compliance to a research protocol is limited in time. Moreover, increasing the number of trials with a participant prone to muscular fatigue can result in major methodological bias because fatigue results in gait pattern modification.

For these reasons, the use of a large force plate on which a subject may place at least two successive steps ensures ground reaction force measurement for all trials and allows investigators to record data for numerous footsteps while avoiding the "targeting" problem. This comes with the drawback of needing to decompose the GRF for each footprint. One prior art method has been developed to decompose the left and right GRF profiles from the global values of the GRFs measured with a single large force plate. This method was based on the examination of the side-to-side oscillations of the global center of pressure (COP) corresponding to the measured global GRF. Despite the fact that this method is often referred for the decomposition of superimposed vertical GRF into left and right force profiles during gait on a treadmill, several points of this method remain unclear and/or difficult to implement. Major assumptions are necessary in order to apply this method: the time samples at which the double and single support phases begin and end must be defined based on a visual inspection of the measured COP plot, which may not be reliable; the method was based on the assumptions that the definition of the start and end of the stance phases is based on these side-to-side oscillations, which were invalidated. Specifically, this point imposes to assign a threshold and define a boundary between double and single stances based on the COP path, but in numerous cases, medio-lateral position of the COP does not systematically show a clear side-to-side inflection point. Furthermore, this method may be questionable if used for children since their gait pattern differs from adults one and is also known as being more variable than for adults, which in turn increases the variability of the side-to-side oscillations of the global COP.

Therefore, there is a need for an improved method and system for decomposing a group reaction force into foot force profiles.

SUMMARY

In accordance with a first broad aspect, there is provided a computer-implemented method for decomposing a ground reaction force (GRF) into individual force profiles, comprising: receiving a time measurement of a global GRF measured while a subject having at least two support contacts for abutting a force platform performs at least one movement on the force platform, the movement comprising at least two motion configurations and each movement configuration being characterized by a respective number of said at least two support contacts being in physical contact with the force platform; identifying individual time regions contained in the time measurement of the global GRF and assigning a respective one of the at least two motion configurations to each time region using a logical order of motion configurations and an identification of a reference motion configuration, thereby identifying the motion configurations contained in the time measurement of the global GRF; for each time region, determining an individual GRF for each one of the at least two support contacts using the identification of the motion configuration for the time region and the time measurement of the global GRF, thereby determining a contribution of each one of the at least two support contacts to the global GRF; and outputting the individual GRFs.

In one embodiment, the logical order of motion configuration comprises a sequence of motion configurations to be executed by the subject on the force platform.

In one embodiment, the logical order of motion configuration further comprises an identification of the support contacts that are in physical contact with the force platform for each motion configurations contained in the logical order.

In one embodiment, the reference motion configuration comprises one of a first motion configuration and a last motion configuration.

In one embodiment, the step of determining an individual GRF is performed using one of: at least one interpolation function; and at least one parametric equation.

In one embodiment, the subject comprises two support contacts, the step of identifying individual time regions comprising determining single stance regions and double stance regions within the global GRF; the step of assigning comprising: assigning a first foot considered as being in contact with the force platform to a first single stance region and assigning the first foot to each subsequent odd single stance region; assigning a second foot considered as being in contact with the force platform to the second single stance region, the first foot being considered to be away from the force platform, and assigning the second foot to each subsequent even single stance region; and the step of determining an individual GRF comprising: for each odd single stance region, assigning a corresponding value of the global GRF to a force of the first foot and a substantially zero value to a force of the second foot; for each even single stance region, assigning a corresponding value of the global GRF to the force of the second foot and the substantially zero value to the force of the first foot; and for each double stance value, determining a first value for the force of the first foot and a second value for the force of the second foot, the sum of the first and second values being equal to the value of the global, thereby obtaining individual foot force profiles.

In one embodiment, the step of determining the single and double stance regions comprises: determining a squared Euclidian norm $\Delta COP^2_{k,l}$ between two sample points k and l using the global GRF; comparing $\Delta COP^2_{k,l}$ to a first threshold; determining a beginning of a double stance region when $\Delta COP^2_{k,l}$ is greater than the first threshold; comparing $\Delta COP^2_{k,l}$ to a second threshold; and determining a beginning of a single stance region when $\Delta COP^2_{k,l}$ is less than the second threshold.

In one embodiment, the method further comprises: determining a squared Euclidian norm $\Delta COP^2_{k,s}$ between the sample points k and a predetermined number s of measurement points using the global GRF, s being greater than one; comparing $\Delta COP^2_{k,s}$ to a third threshold; and predicting that a squared Euclidian norm peak will occur within the predetermined number s of measurement points.

In one embodiment, the step of determining the single and double stance regions comprises: determining the peak points in time at which a GRF peak occurs; determining a squared Euclidian norm $\Delta COP^2_{k,l}$ between two sample points k and l using the global GRF; and starting from each peak point in time, determining a first last point in time for which $\Delta COP^2_{k,l}$ is greater than a first threshold, the first last point in time separating a first single stance region from a given double stance region, and determining a second last point in time for which $\Delta COP^2_{k,l}$ is less than a second threshold, the second last point in time separating the given double stance region from a second single stance region.

In one embodiment, the method further comprises determining the identification of the reference motion configuration using a lateral displacement in time of a global center of pressure.

In accordance with a second broad aspect, there is provided a system for decomposing a ground reaction force (GRF) into individual force profiles, comprising: a stance region determining module for: receiving a time measurement of a global GRF measured while a subject having at least two support contacts for abutting a force platform performs at least one movement on the force platform, the movement comprising at least two motion configurations and each movement configuration being characterized by a respective number of said at least two support contacts being in physical contact with the force platform; identifying individual time regions contained in the time measurement of the global GRF and assigning a respective one of the at least two motion configurations to each time region using a logical order of motion configurations and an identification of a reference motion configuration, thereby identifying the motion configurations contained in the time measurement of the global GRF; and an individual GRF determining module for: for each time region, determining an individual GRF for each one of the at least two support contacts using the identification of the motion configuration for the time region and the time measurement of the global GRF, thereby determining a contribution of each one of the at least two support contacts to the global GRF; and outputting the individual GRFs.

In one embodiment, the logical order of motion configuration comprises a sequence of motion configurations to be executed by the subject on the force platform.

In one embodiment, the logical order of motion configuration further comprises an identification of the support contacts that are in physical contact with the force platform for each motion configurations contained in the logical order.

In one embodiment, the reference motion configuration comprises one of a first motion configuration and a last motion configuration.

In one embodiment, the individual GRF determining module is adapted to determine the individual GRF using one of: at least one interpolation function; and at least one parametric equation.

In one embodiment, the subject comprises two support contacts, the stance region determining module being adapted to: determine single stance regions and double stance regions within the global GRF; assign a first foot considered as being in contact with the force platform to a first single stance region and assigning the first foot to each subsequent odd single stance region; assign a second foot considered as being in contact with the force platform to the second single stance region, the first foot being considered to be away from the force platform, and assigning the second foot to each subsequent even single stance region; and the individual GRF determining module is adapted to: for each odd single stance region, assign a corresponding value of the global GRF to a force of the first foot and a substantially zero value to a force of the second foot; for each even single stance region, assign a corresponding value of the global GRF to the force of the second foot and the substantially zero value to the force of the first foot; and for each double stance value, determine a first value for the force of the first foot and a second value for the force of the second foot, the sum of the first and second values being equal to the value of the global, thereby obtaining individual foot force profiles.

In one embodiment, the stance region determining module being adapted to: determine a squared Euclidian norm $\Delta COP^2_{k,l}$ between two sample points k and l using the global GRF; compare $\Delta COP^2_{k,l}$ to a first threshold; determine a beginning of a double stance region when $\Delta COP^2_{k,l}$ is greater than the first threshold; compare $\Delta COP^2_{k,l}$ to a second threshold; and determine a beginning of a single stance region when $\Delta COP^2_{k,l}$ is less than the second threshold.

In one embodiment, the stance region determining module is further adapted to: determine a squared Euclidian norm $\Delta COP^2_{k,s}$ between the sample points k and a predetermined number s of measurement points using the global GRF, s being greater than one; compare $\Delta COP^2_{k,s}$ to a third threshold; and predict that a squared Euclidian norm peak will occur within the predetermined number s of measurement points.

In one embodiment, the stance region determining module is further adapted to: determine the peak points in time at which a GRF peak occurs; determine a squared Euclidian norm $\Delta COP^2_{k,l}$ between two sample points k and l using the global GRF; and starting from each peak point in time, determine a first last point in time for which $\Delta COP^2_{k,l}$ is greater than a first threshold, the first last point in time separating a first single stance region from a given double stance region, and determine a second last point in time for which $\Delta COP^2_{k,l}$ is less than a second threshold, the second last point in time separating the given double stance region from a second single stance region.

In one embodiment, the stance region determining module is further adapted to determine the identification of the reference motion configuration using a lateral displacement in time of a global center of pressure.

In accordance with another broad aspect, there is provided a system for measuring a ground force reaction (GRF), comprising: a force platform provided with at least one sensor for measuring a global GRF while a subject having at least two support contacts for abutting a force platform performs at least one movement on the force platform, the movement comprising at least two motion configurations and each movement configuration being characterized by a respective number of said at least two support contacts being in physical contact with the force platform; a stance region determining module for: receiving a time measurement of a global GRF from the force platform, identifying individual time regions contained in the time measurement of the global GRF and assigning a respective one of the at least two motion configurations to each time region using a logical order of motion configurations and an identification of a reference motion configuration, thereby identifying the motion configurations contained in the time measurement of the global GRF; and an individual GRF determining module for: for each time region, determining an individual GRF for each one of the at least two support contacts using the identification of the motion configuration for the time region and the time measurement of the global GRF, thereby determining a contribution of each one of the at least two support contacts to the global GRF; and outputting the individual GRFs.

It should be understood that a subject may be any entity provided with at least two support contacts and adapted to move on a force platform. For example, a subject may be a human being having two feet. In another example, a subject may be a one-legged human being walking with a single crutch or a cane. In a further embodiment, a subject may be a human being having two feet and walking with a walking frame or two crutches. It should be understood that a subject may also be an entity other than a human being such as an animal, a robot, or the like. For example, the subject may be a horse, a dog, etc.

The support contacts are the parts of the subject that abuts on the surface on which the subject moves during the movement of the subject thereon. Examples of support contacts comprise a foot, a paw, an end of a crutch adapted to be abutted on a floor, a wheel of a walking frame, an end of a walking frame adapted to abut a floor, etc. It should be understood that the number of support contacts may vary from one subject to another and is greater or equal to two. In an example in which the subject is a biped entity, the subject comprises two support contacts such as two feet, one feet and one crutch, two paws, or the like. In an example in which the subject has two legs and is provided with a crutch, the subject comprises three support contacts, i.e. the subject's two feet and the crutch. In another example in which the subject has two legs and is provided with two crutches, the subject comprises four support contacts, i.e. the subject's two feet and the two crutches. Other examples of a subject having four support contacts comprise mammals such as dogs, cats, horses, etc.

A configuration of the subject is characterized by the number of support contacts that abut the surface. For example, during a given configuration for a human being having two legs, only one of the two feet may be in physical contact with the ground while the other feet is away from the ground. This configuration is referred to as a single stance configuration. In another configuration, the two feet of the human being may be physical contacts with the ground. This further configuration is referred to as a double stance configuration. In a further configuration, the two feet of the human being may away from the ground such as during a jump.

During a motion, a subject passes a start configuration to at least another configuration. Therefore, a configuration comprises at least two configurations. The at least two configurations may be of a same type. For example, the two configurations may both be single stance configurations such as when a human being jumps from one foot to the other. In the single stance configuration only one foot of the human being, i.e. the right foot or the left foot, is in contact with the ground while the other foot is away from the ground. The at least two configurations may also be of different types. For example, a walking motion for a human being comprises single stance configurations and double stance configurations. In the double stance configurations, both the right and left feet of the human being are in physical contact with the ground.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
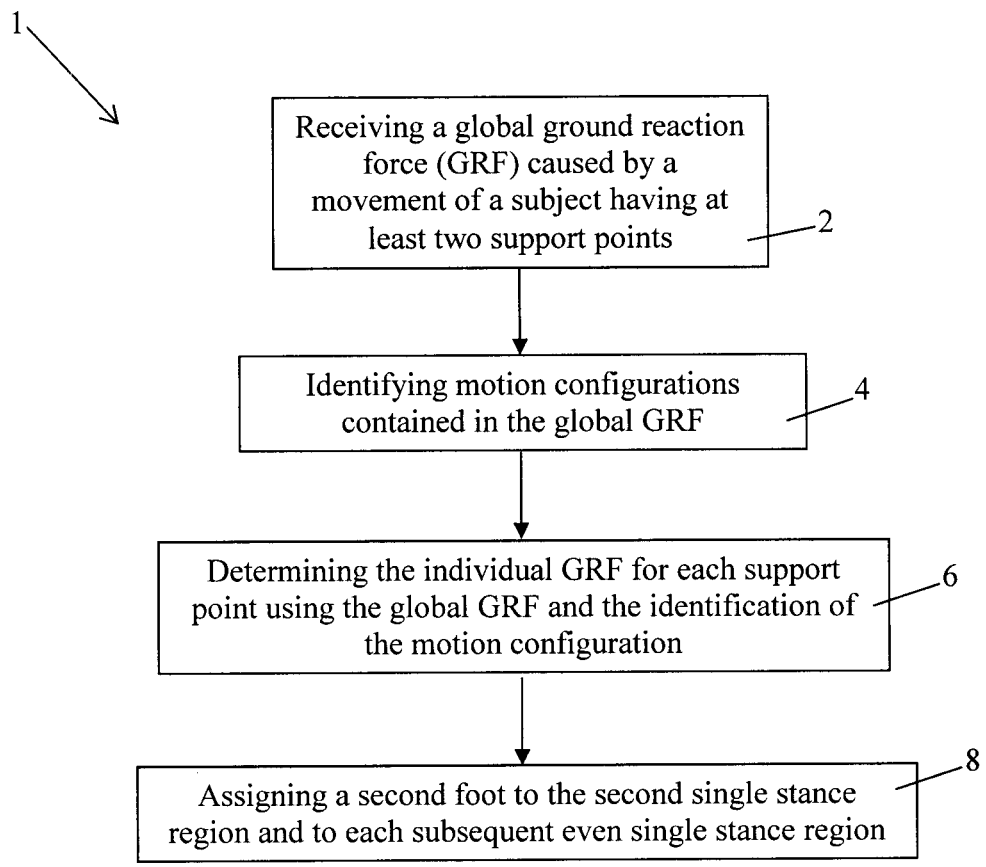
FIG. 1 is a flow chart of a method for decomposing a global GRF into individual force profiles, in accordance with an embodiment.

FIG. 1 illustrates one embodiment of a method 1 for decomposing a global GRF into individual forces. The global GRF is measured while a subject is moving on a force platform. The movement of the subject comprises at least two motion configurations. The force platform is provided with at least one force sensor for measuring the global GRF while the subject is moving thereon. The size of the force platform is chosen so as to allow the subject to place at least two successive steps thereon. The global GRF corresponds to the summation of the GRFs caused by all of the support contacts of the subject. As described above, the measurement of the global GRF as a function of time comprises different time regions each corresponding to a respective motion configuration.

At step 2, a time measurement of the global GRF while the subject moves on the force platform is received from the force platform that is provided with at least one sensor adapted to measure the global GRF. The movement of the subject comprises at least two motion configurations, which may be of a same type or not. For each motion configuration, a respective number of support contacts of the subject are in physical contact with the force platform.

At step 4, individual time regions of the measurement of the global GRF are identified and a respective motion configuration is assigned to each time region, thereby identifying the different motion configurations contained in the time measurement of the global GRF. An identification of the support contacts of the subject, which are in physical contact with the force platform for each time region, is further performed at step 4 using a logical order for the motion configurations. The logical order for the motion configurations is indicative of the sequence of motion configurations and an identification of their respective support contacts, which are in physical with the force platform during the respective motion configuration. Taking the example of the human being walk, a logical order of motion configurations may be: (single stance, right foot), (double stance, right and left feet), and (single stance, left foot). In an embodiment in which all of the motion configurations during the motion of the subject are of different types, the logical order may not comprise any identification of the physical support contacts that abut the force platform during each motion configuration. For example, if the motion comprises the motion configuration (single stance, left foot), (triple stance, left foot and crutches), and (double stance, crutches), then the motion configurations are all of different types, and the identification of the physical support contacts is not necessary to assign a motion configuration each time region. In this case, the reference motion configuration such as the first configuration comprises an identification of a given motion configuration such as single stance or double stance included in the logical order, and may not comprise an identification of the physical support contact(s) that abut(s) the force platform during the reference motion configuration.

In one embodiment, the logical order of motion configurations comprises a motion cycle, i.e. a sequence of motion configurations, which may be repeated during the measurement of the global GRF.

In one embodiment, the subject starts the movement on the force platform by a reference motion configuration. The reference motion configuration is indicative of the number and the identification of the support contacts, which are in physical contact with the force platform. Since the logical order of the motion configurations and the first motion configuration of the movement, i.e. the reference motion platform, are known, it is possible to assign a respective motion configuration and respective support contacts that are in physical contact with the force platform to each previously determined time region.

In another embodiment, the method 1 further comprises a step of receiving an identification of the first motion configuration performed by the subject and an identification of the support contacts of the subject actually in physical contact with the force platform during the first motion configuration. Since the logical order of the motion configurations and the first motion configuration of the movement are known, it is possible to assign a respective motion configuration and respective support contacts that are in physical contact with the force platform to each time region.

In one embodiment, the squared Euclidian norm $\Delta COP^2_{k,l}$ between two measurement/sample points k and l of the global GRF is calculated and the determination of the motion configurations is performed according to $\Delta COP^2_{k,l}$, as described in greater detail below. Each local extrema of $\Delta COP^2_{k,l}$ is indicative of a frontier between two successive motion configuration. Therefore, each time region contained between two successive extrema corresponds to a given motion configuration.

Once each time region has been assigned a respective motion configuration and respective support contacts in physical contact with the force platform during the respective motion configuration, the next step 6 consists in determining, for each time region, the contribution of each support contact to the global GRF, i.e. the individual GRFs each caused a respective support contact. As described in further detail below, interpolation may be used to determine the individual GRFs. It should be noted that the contribution of a given support contact which is away from the force platform during a given time region to the global GRF is null, i.e. the value of the individual GRF for the given support contact is null. It should also be noted that for each motion configuration for which a single support contact in physical contact with the force platform, the whole value of the global GRF is assigned to the single support point.

At step 8, the individual GRFs for the support contacts are outputted, i.e. the value of the GRF in time for each support contact is outputted.

Figure 2:
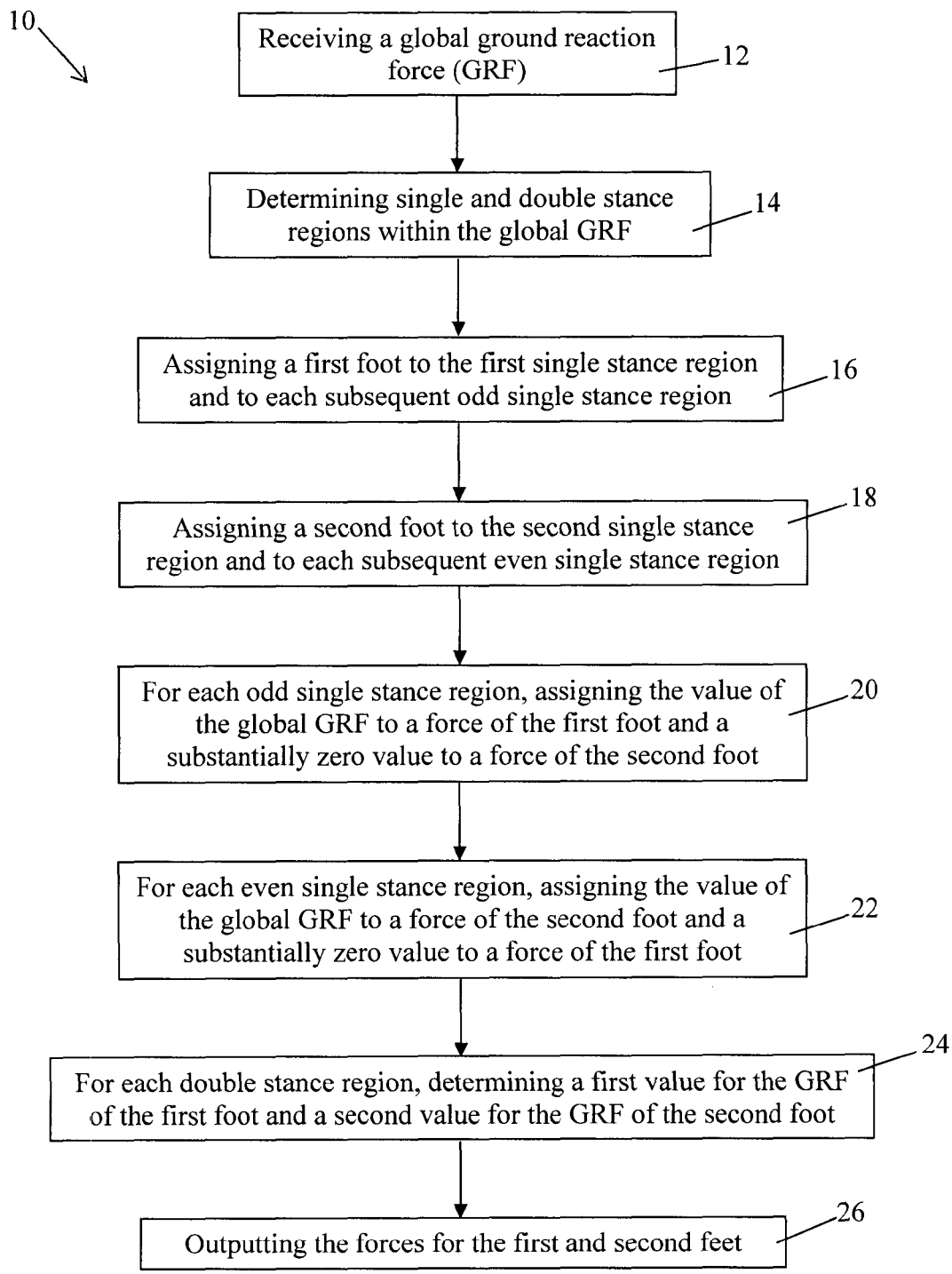
FIG. 2 is a flow chart of a method for decomposing a global GRF into two individual foot force profiles for a subject walking on a force platform, in accordance with an embodiment.

FIG. 2 illustrates one embodiment of a method 10 for decomposing a global GRF into individual foot forces and corresponds to an application of the method 1 to a biped subject provided with a right and left support contacts such as a human being having a right foot and a left foot. The global GRF is measured while a subject is moving on a force platform, e.g. running or walking on the force platform. The force platform is provided with at least one force sensor for measuring the global GRF while the subject is moving on the force platform. The size of the force platform is chosen so as to allow the subject to place at least two successive steps thereon. The global GRF comprises the GRF caused by the right foot of the subject and that caused by the left foot of the subject. As described below, the measurement of the global GRF as a function of time comprises two types of time regions: single stance regions and double stance regions. During a single stance region, only one foot of the subject is in physical contact with the force platform while the other foot is away from the force platform. Therefore, only the foot that is in contact with the force platform contributes to the global GRF in a single stance region.

During a double stance region, both feet of the subject are in physical contact with the force platform. In this case, the global GRF is the sum of the GRF caused by the right foot ant that caused by the left foot.

It should be understood that the GRF and global GRF referred to in the present description comprise a GRF in time and a global GRF in time, respectively.

At step 12, the value of the measured GRF as a function of time is received. The global GRF corresponds to the GRF measured as a function of time by the sensor(s) of the force platform while the subject is moving thereon. The global GRF corresponds to the summation of the GRF caused by the left foot of the subject and the GRF caused by the right foot of the subject. In one embodiment, the global GRF comprises a global vertical GRF, i.e. the vertical component of the global GRF. In another embodiment, the global GRF comprises a global transverse GRF, i.e. one transverse component of the global GRF. In a further embodiment, the global GRF comprises three global GRF components, i.e. a vertical GRF component and two transverse global GRFs.

In one embodiment, the global GRF is received in substantially real-time from the force platform while the subject moves on the force platform and the force platform measures the global GRF. In this case, each time the force platform measured a global GRF, the value of the measured GRF is transmitted. In another embodiment, the global GRF is received after the subject has moved on the force platform. In this case, all of the values for the measured global GRF are concurrently transmitted after the subject has completed his motion on the force platform.

At step 14, the single stance and double stance regions comprised in the global GRF are determined using an identification of the first configuration, an identification of the foot/feet that is/are in physical contact with the force platform during the first configuration, and a cyclic and ordered sequence of motion configurations which is: (single stance, left foot); (double stance, left and right feet), and (single stance, right foot). As a result, a plurality of single stance regions during which only one foot of the subject is in contact with the force platform are identified, and at least one double stance region during which both feet of the subject are in contact with the force platform are identified. It should be understood that any adequate method for determining the single and double stance regions may be used.

In one embodiment and as described below, the squared Euclidian norm $\Delta COP^2_{k,l}$ between two measurement/sample points k and l of the global GRF is calculated and the determination of the single and double stance regions is performed according to $\Delta COP^2_{k,l}$. In an embodiment in which the determination of the signal and double stance regions is done in substantially real time, each time the force platform measured a value of the global GRF, the measured value point is transmitted and $\Delta COP^2_{k,l}$ is calculated. In this case, the method for determining the single and double stance regions comprises three steps. The first step consists in predicting when a $\Delta COP^2$ peak will occur within a predetermined number s of measurement sample points. In order to do so, $\Delta COP^2_{k,s}$ is compared to a first constant threshold $C_P$. When $\Delta COP^2_{k,s}$ is greater that the threshold constant $C_P$, then it is determined that the beginning of a $\Delta COP^2$ peak will occur within the next s sample points. At a second step, $\Delta COP^2_{k,l}$ is compared to a second threshold constant $C_F$. The first point in time $t_1$ at which becomes $\Delta COP^2_{k,l}$ greater than $C_F$ is determined as being the frontier between a single stance region (for $t<t_1$) and a double stance region (for $t \geq t_1$). The end point in time $t_2$ of the double stance region is determined by comparing $\Delta COP^2_{k,l}$ to a third threshold constant $C_L$. The first point in time for which $\Delta COP^2_{k,l}$ is lower than $C_L$ is determined as being the beginning of a next single stance region. Therefore, the double stance region extends between $t_1$ and $t_2$, and is sandwiched between two single stance regions.

In one embodiment, the step of comparing $\Delta COP^2_{k,s}$ to the first constant threshold $C_P$ is omitted. In this case, only $\Delta COP^2_{k,l}$ is compared to the threshold constants $C_F$ and $C_L$ in order to differentiate the singles and double stance regions. In one embodiment, the step of comparing $\Delta COP^2_{k,s}$ to the first constant threshold $C_P$ is performed in order to increase the robustness of the detection of the single and double stance regions.

It should be understood that the above-described method for determining the single and double stance regions may be performed substantially in real-time while the subject moves on the force platform. It should be understood that the inclusion of the step of comparing $\Delta COP^2_{k,s}$ to $C_P$ induces a delay equivalent to the computation of s sample points. Alternatively, the method may be performed after the subject has moved on the force platform.

Figure 4:
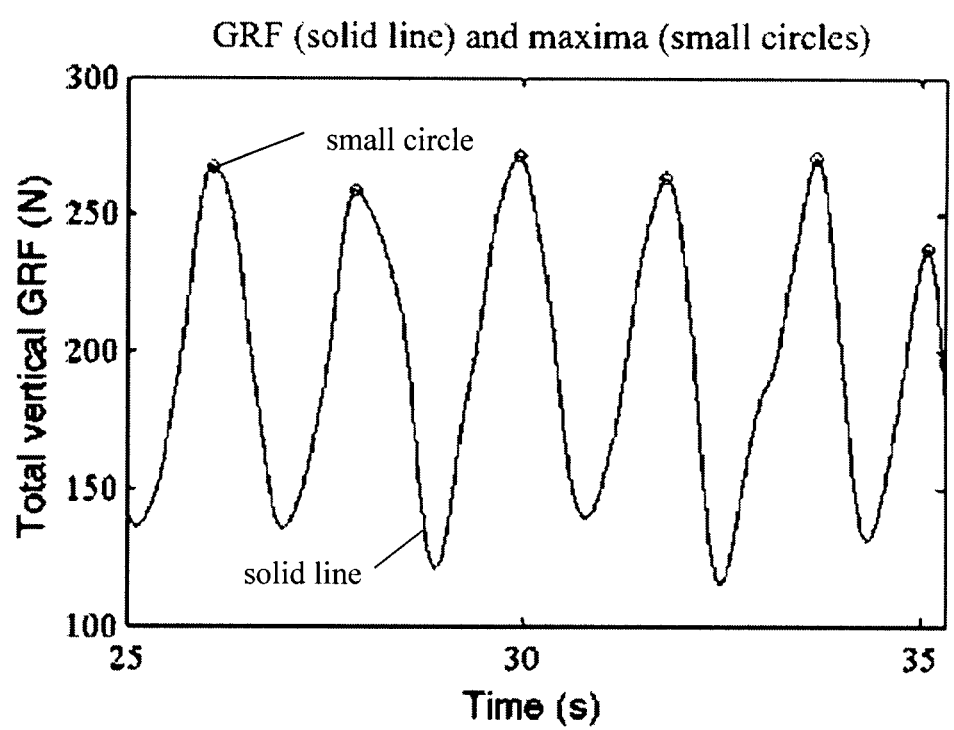
FIG. 4 is an exemplary graph of a global vertical GRF as a function of time.

In another embodiment, the determination of the single and double stance regions is done by first identifying the points in time $t_{max}$ at which a global GRF peak occurs, as illustrated in FIG. 4 which presents the total vertical GRF (solid line) and the corresponding maxima (small circles). Each GRF peak is considered to be located within a double stance region. As for the previous method, $\Delta COP^2_{k,l}$ is determined from the global GRF for each time point. Starting from the point in time $t_{max}$, the boundaries of the double stance region are determined by comparing $\Delta COP^2_{k,l}$ to the threshold constants $C_F$ and $C_L$. Starting from $t_{max}$, the last point in time $t_1$ for which $t<t_{max}$ and $\Delta COP^2_{k,l}>C_F$ is identified as being the beginning of the double stance region. Starting from $t_{max}$, the first point in time $t_2$ for which $t>t_{max}$ and $\Delta COP^2_{k,l}<C_F$ is identified as being the end of the double stance region. As a result, the double stance region extends between $t_1$ and $t_2$, and is sandwiched between two single stance regions.

In one embodiment, the detection of the global GRF peaks is limited to the portion of the global GRF that complies with the following equation:

$$\text{Global GRF} > \text{mean(global GRF)} + x.\text{SD(global GRF)} \quad \text{Eq. 1}$$

where SD stands for standard deviation and x is a positive number. For example, x may be equal to 1. In this case, the search for the GRF peaks is limited to only 15.8% of the sample points. In another example, x may be equal to 2. In this case, the search for GRF peaks is limited to only 2.2% of the sample points.

In one embodiment, the period, i.e. the time duration between two successive GRF peaks, is determined. For example, the period may be the mean of all of the time durations between two successive GRF peaks. Then, for each period centered on a respective GRF peak, it is determined whether another peak complying with Eq. 1 may be found. If no other GRF peak may be found, then the respective GRF peak that is centered on the period is confirmed as being the GRF peak. If at least another peak is found within the period, then only the GRF peak having the greatest amplitude is kept and is identified as being the GRF peak for the period. This embodiment allows for robustness in the detection of the GRF peaks.

Referring back to the method 10, the next step 16 comprises assigning a first foot identification to the first single stance region. The same first foot identification is assigned to each odd single stance region. If the first single stance region is assigned the first foot, i.e. only the first foot is in contact with the force platform during the first stance region, then the third single stance region is assigned the first foot, the fifth single stance region is assigned the first foot, etc.

At step 18, the second foot identification is assigned to the second single stance region. The same second foot identification is also assigned to each even single stance region. If the second single stance region is assigned the second foot, i.e. only the second foot is in contact with the force platform during the second stance region, then the fourth single stance region is assigned the second foot, the sixth single stance region is assigned the second foot, etc.

At step 20, for each odd single stance region, the value of the global GRF is assigned to the GRF caused by the first foot and a zero value is assigned for the GRF caused by the second foot, since the second foot is not in contact with the force platform during an odd single stance region and cannot therefore contribute to the global GRF.

At step 22, for each even single stance region, the value of the global GRF is assigned to the GRF caused by the second foot and a zero value is assigned for the GRF caused by the first foot, since the first foot is not in contact with the force platform during an odd single stance region and cannot therefore contribute to the global GRF.

At step 24, for each double stand region, the value of the GRF caused by the first foot and the value of the GRF caused by the second foot are determined. In one embodiment, an interpolation method is used. Taking the example of the first and second single stand regions and the first double stand region, interpolation is used for determining the value of the GRF caused by the first foot within the first double stand region to match the value of the GRF caused by the first foot within the first single stand region and that within the second singled stand region. In other words, the contribution of the GRF caused by the first foot to the global GRF is determined using any adequate interpolation method. Since the global GRF value is equal to the sum of the GRF value for the first foot and that for the second foot, the value of the GRF for the second foot may be obtained by subtracting the determined GRF value for the first foot from the global GRF. In another example, the GRF caused by the second foot may first be determined by interpolation and then the GRF caused by the first foot may then be calculated using the global GRF and the determined GRF for the second foot. The GRFs for the first and second feet form the foot force profiles. It should be understood that any adequate interpolation method may be used to determine the contribution of the first foot and/or the second foot to the global GRF. For example, polynomial interpolation or spline interpolation may be used. In another example, parameterization may be used as an interpolation method. In this case, a parametric function is used for assessing the value of the GRF caused by the first or second foot during a double stand region.

At step 26, the determined foot force profiles are outputted, each with an indication of their respective foot, i.e. an indication of the first or second foot. The foot force profiles may be stored in memory, displayed to a user, converted into graphical representation and optionally displayed to the user, etc.

In one embodiment, the subject is asked to always start by landing a given foot on the force platform. In this case, it is determined that the first foot to be in contact with the force platform is always the given foot. For example, the subject may be asked to start by landing the right foot on the force platform. In this case, the right foot is assigned to all of the odd single stand regions, and the left foot is assigned to all of the even single stand regions.

In another embodiment, the method further comprises receiving a right or left foot identification for a reference single stand region, such as the first single stand region or the last single stand region, and assigning a respective one of the right and left foot to the first and second feet. For example, an indication that the right foot landed first on the force platform may be received. In this case, the right foot corresponds to the first foot and the left foot corresponds to the second foot. In one embodiment, the assignment to the right or left foot to the first and second feet is performed concurrently with the determination of the foot force profiles. In another embodiment, the assignment to the right or left foot to the first and second feet is performed after the determination of the foot force profiles and before the outputting of the foot force profiles.

In a further embodiment, the method further comprises a step of identifying the foot that is in physical contact with the force platform during a reference single stance region such as the first single stance region. The identification of the given foot is performed by determining a lateral displacement in time of the global center of pressure. If during the reference single stance region, the global center of pressure laterally moves leftward, then it is determined that the left foot is in physical contact with the force platform during the reference single stance region. If during the reference single stance region, the global center of pressure laterally moves rightward, then it is determined that the right foot is in physical contact with the force platform during the reference single stance region.

In one embodiment, the method 10 is applied to the global vertical GRF. In this case, only the vertical component of the global GRF is used in the method 10 and the determined foot force profiles correspond to the vertical component of the GRF caused by the first and right feet, i.e. the right and left feet.

In another embodiment, the method 10 is applied to the global transverse GRF which corresponds to a transverse component of the global GRF. In this case, only the transverse component of the global GRF is used in the method 10 and the determined foot force profiles correspond to the transverse component of the GRF caused by the first and right feet, i.e. the right and left feet.

In a further embodiment, the method 10 is applied to the components according to three axes of the global GRF, such as the vertical component and two transverse components of the global GRF. The total GRFs for the first and the second feet can then be determined from the vertical GRF and the two transverse GRF for the first and the second feet. In this case, the method 10 is applied three times. The method 10 is applied to the global vertical GRF in order to determine the contributions of each foot to the global vertical GRF, to one of the two global transverse GRF to determine the contribution of each foot to the first global transverse GRF, and to the other global transverse GRF to determine the contribution of each foot to the second global transverse GRF.

While the method 10 is an example of the application of the method 1 to a biped subject, it should be understood that the method 1 may be applied to a subject having more than two support contact such as a person walking with a single crutch or cane.

Figure 3:
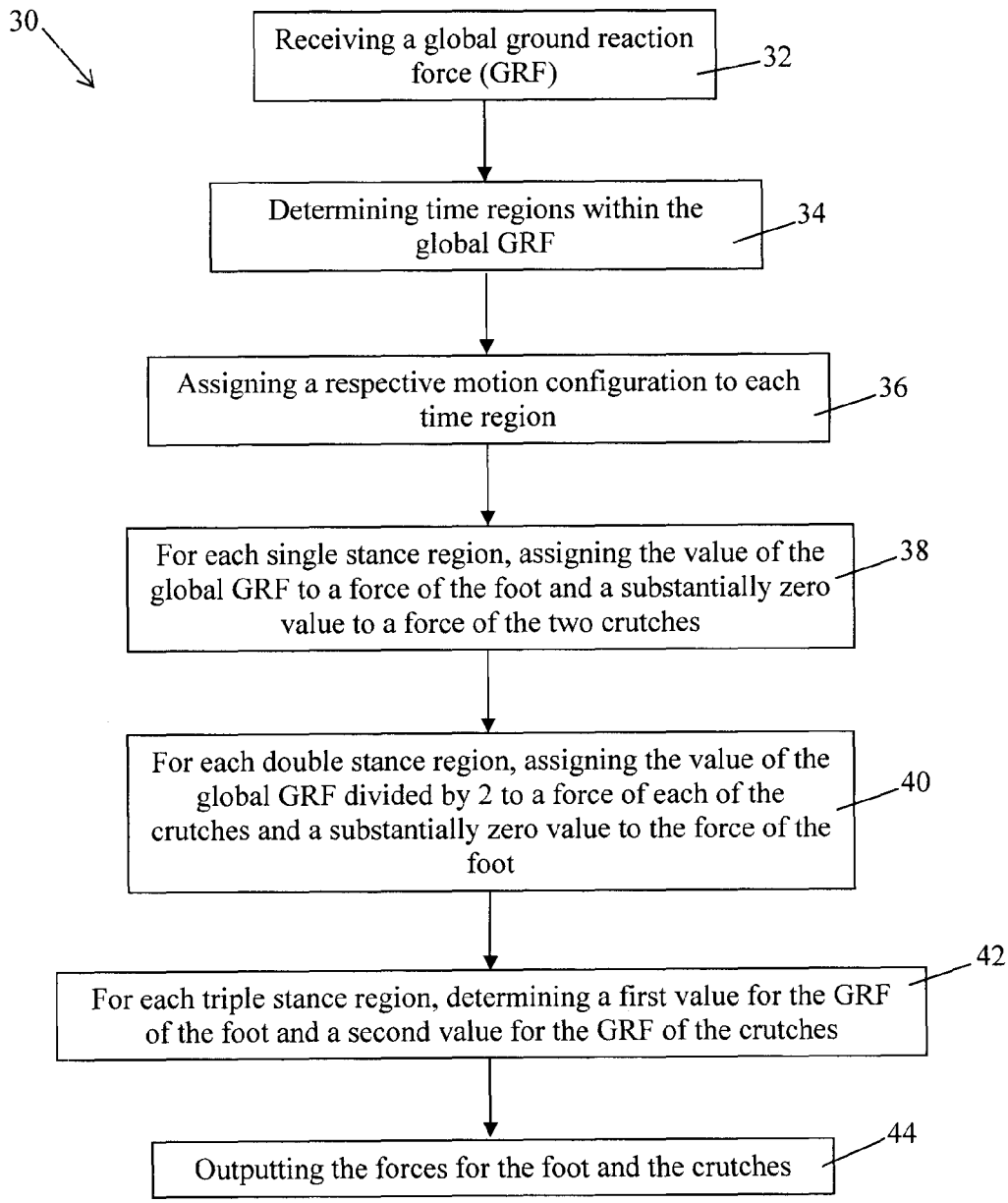
FIG. 3 is a flow chart a method for decomposing a global GRF into two individual force profiles for a subject walking on a force platform with a pair of crutches, in accordance with an embodiment.

FIG. 3 illustrates one embodiment of a method 30 for decomposing a global GRF into individual forces and corresponds to an application of the method 1 to a biped subject provided with one support contact, such as a right or left foot, and two crutches. For example, the subject may walk on the force platform while his left foot never stands on the force platform. In this case, the subject is provided with three support contacts, i.e. the right foot and the two crutches.

In this case, the logical order of the motion configurations during the walk of the subject using the crutches is the following: (single stance, right foot), (triple stance, right foot and crutches), and (double stance, the two crutches). This sequence of motion configurations may be cyclically repeated during the walk of the subject on the force platform.

At step 32, the global GRF, i.e. a time measurement of the global GRF while the subject walks on the force platform, is received from the force platform.

At step 34, the time measurement of the global GRF is divided into individual time regions each corresponding to a respective stance configuration, using the above-described method. At step 36, a respective motion configuration is assigned to each time region using the above-described logical order of motion configurations and an identification of the first motion configuration performed by the subject during his walk on the force platform, as described above.

At step 38, for each single stance region, the value of the global GRF is assigned to the right foot which is in physical contact with the force platform during the single stance configuration, and the value of the GRF for each crutch is set to zero.

At step 40, for each double stance region, the value of the global GRF is splitted between the two crutches, and a zero GRF value is assigned to the right foot. In one embodiment, half of the global GRF is assigned to the GRF value of the first crutch, such as the right crutch, and the other half of the value of the global GRF is assigned to the GRF value of the second crutch. While in the present embodiment, the global GRF value is evenly splitted between the two crutches, it should be understood that other embodiments may be possible. For example, 52% of the global GRF value may be assigned to the right crutch while 48% of the global GRF value may be assigned to the left crutch.

At step 42, for each triple stance configuration, a GRF value is determined for the right foot and the two crutches using interpolation as above-described. First, the GRF value of the right foot and the combined GRF value for the two crutches are determined using the above-described method. Then, the combined GRF value for the two crutches is splitted into a GRF value for the left crutch and a GRF value for the right crutch. For example, the combined GRF value for the two crutches may be evenly splitted between the two crutches.

At the end of step 42, the GRF value for each support contact is known for each time region, and the individual force profile for each support contact is obtained by combining together the value of the GRF of the support contact for each time region.

At step 44, the individual force profiles are outputted.

In the following, experimental results are provided.

Six typically developing children were included in the present study (height: 1.38 m (SD: 0.18); weight: 35.1 kg (SD: 11.1), equivalent to 344.3 N (SD: 108.9), and age: 9.3 years (SD: 2.9, range: 6-13)). Exclusion criterion was known orthopedic surgical intervention during the last 6 months.

A strain gauge platform (1.8 m long and 0.6 m wide), made of seven force plates of different sizes was mounted at ground level in the middle of a walkway (10 m long). Each of the seven force plates was composed by force sensors recording three-dimensional force components. Each of the seven force plates had its own processor. The processors were triggered and synchronized together. The three components of GRF, i.e. the vertical component and two transverse components, were measured at the four edges of each force plate, at a sampling frequency, fe, equal to about 50 Hz. In one embodiment, the above-described set-up allows to record forces during untargeted gait in the walkway, enabling to obtain independent left-right GRFs without targeting steps on the force platforms, and avoiding repeating trials.

While in the presented experiment, a force platform formed of seven force plates was used in order to compare the present method which does not require a target gait, to the usual method in which targeted gait is required, it should be understood that the present method may be used with a single force platform such as a set-up comprising a single force plate positioned underneath a treadmill belt. The present method may also be used with a force platform comprising a plurality of force plates. In this case, targeted gait for the subject is not required.

In one embodiment, photocells were placed at each end of the force platform set-up and at the neck level of the participants. These photocells were used to assess gait regularity during the trials: the trials demonstrating a clear trend towards a velocity increase or decrease were discarded according to Tesio's criterion (i.e. a velocity variation superior to 40%).

The participants were instructed to look straight ahead and to walk as naturally as possible in the walkway. Practically, all subjects walked over the force platforms wearing their clothes and shoes. No feedback information was given to the participants during the trials.

Trials were selected for analysis only if the participant placed two consecutive steps on independent force plates (i.e. left and right feet were not placed on the same force plate), and with no foot contact outside of the force plate surface. Finally, for each of these selected trials, the vertical components of the GRFs measured on the independent force plates, on which the participant placed their feet, were numerically summed after recording in order to obtain the corresponding global vertical GRF. Then, the above-described decomposition method was applied to the global vertical GRF in order to obtain the foot force profiles. The validation consisted in comparing the vertical GRFs computed from the decomposition to the original independently measured vertical GRFs.

Six double stances performed by each of the six typically developing children were included in the data processing, giving a total of 36 double stance phases.

Theoretical Investigation

During the single stances, the global GRF is affected to the corresponding foot that is in contact with the ground, and there is no GRF under the other foot in aerial phase. Consequently, the decomposition of the global GRFs into left-right profiles is only necessary during the double stances. Thus, it is important to detect the exact time steps of transitions between the single and double stances. In order to detect these transitions, we have successively computed the following definitions related to the COP.

COP-related Definitions

On each force plate i=1, . . . , n (where n=7), the local center of pressure, LCOP, related to the system reference point O, can be determined from the $i^{th}$ plate force data, using the following equation:

$$\overrightarrow{OP_i} = (OP_{x_i}, OP_{y_i}, OP_{z_i}) = \left(-\frac{M_{y_i}}{F_{z_i,tot}} + X_i, \frac{M_{x_i}}{F_{z_i,tot}} Y_i, Z_i\right) \quad \text{Eq. 2}$$

where:

the local frames of the platforms are aligned with the global frame, namely X along the anteroposterior direction and positive forward, Y along the mediolateral direction and positive to the left, Z along the vertical axis and positive upward;

$\overrightarrow{OP_i}$ is the vector of the LCOP position on the $i^{th}$ force plate;

i=1, . . . , n is the index of the force plate;

$F_{z_i,tot}$ is the total vertical GRF on the $i^{th}$ force plate;

$M_{x_i}$ and $M_{y_i}$ are antero-posterior and lateral components, respectively, of the resulting moment on the $i^{th}$ force plate, related to the reference O;

$X_i$ and $Y_i$ are the antero-posterior and lateral components, respectively, of the reference point, $O_i$, of the $i^{th}$ force plate, relatively to the global reference O; $X_i$ and $Y_i$ were manually measured for each force plate; and $Z_i$ is the $i^{th}$ force plate height, measured from the reference O; all force platforms being fixed to the floor, $Z_i$ is assumed to be constant and was manually measured for the set-up.

The global center of pressure (GCOP), is defined as the weighted sum of the LCOP on every contact platform. Its expression related to the system referential point O is given by:

$$\overrightarrow{OP} = \frac{\sum_{i=1}^{n} F_{z_i,tot} \cdot \overrightarrow{OP_i}}{\sum_{i=1}^{n} F_{z_i,tot}} \quad \text{Eq. 3}$$

where:

i=1, . . . , n is the index of the force plate; and
$F_{z_i,tot}$ is the vertical force data on the ith platform.

By replacing the variable $\overrightarrow{OP_i}$ in Equation (3) by its formulation given by Equation (2), the GCOP can be determined as follows:

$$\overrightarrow{OP} = \frac{\sum_{i=1}^{n} F_{z_i,tot} \cdot \left(-\frac{M_{y_i}}{F_{z_i,tot}}, \frac{M_{x_i}}{F_{z_i,tot}} \cdot H_i\right)}{F_{z_{tot}}} = \quad \text{Eq. 4}$$

$$\frac{\sum_{i=1}^{n} (-M_{y_i}, M_{x_i}, F_{z_i,tot} \cdot H_i)}{F_{z_{tot}}}$$

where $$F_{z_{tot}} = \sum_{i=1}^{n} F_{z_i tot}$$

and $F_{z_i,tot}$ have been cancelled out from the denominators in order to reduce large inaccuracies of the GCOP calculation when $F_{z_i,tot}$ is low, i.e. at the beginning and the end of each footstep on a force plate i.

Further, Equation (4) appears as a generalization of Equation (2) for several force plates, and this is the formulation that will be considered to compute the GCOP that will be used below.

On the basis of the GCOP, $\Delta COP^2$ is defined as the squared Euclidian norm in the horizontal plane between two sample points k and k+l of the GCOP:

$$\Delta COP^2_{k,l} = (OPx_{k+l} - OPx_k)^2 + (OPy_{k+l} - OPy_k)^2 \quad \text{Eq. 5}$$

Figure 5:
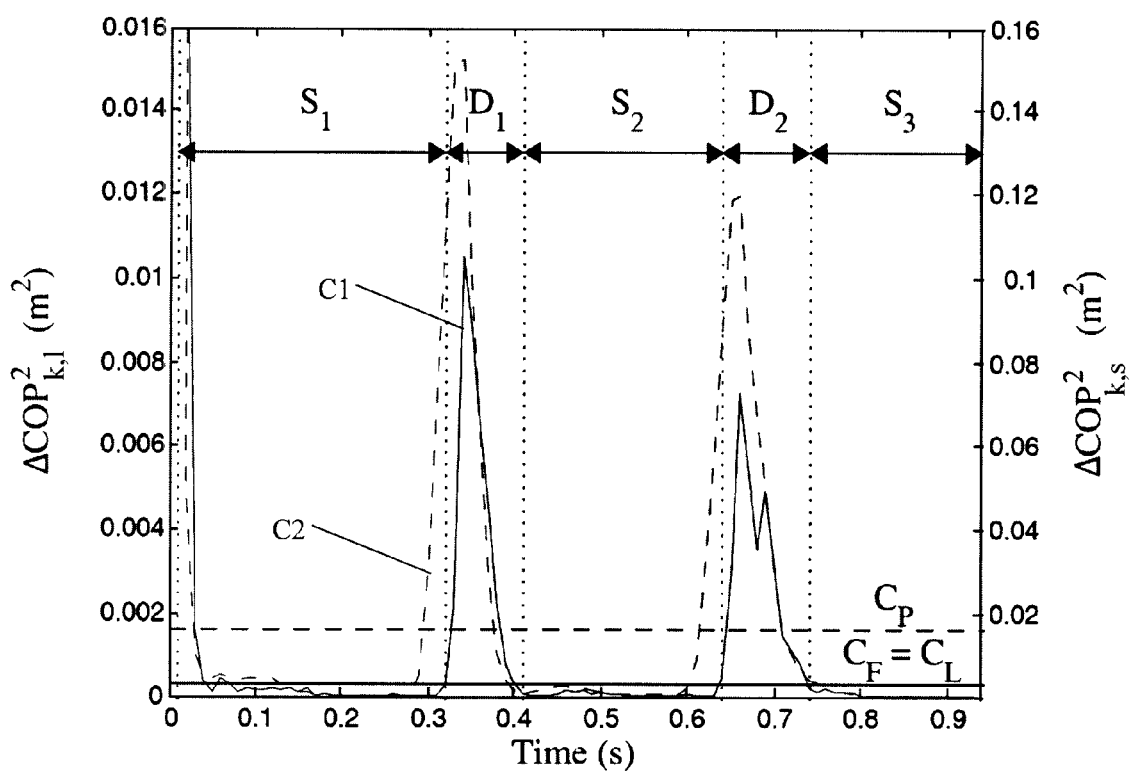
FIG. 5 is an exemplary graph illustrating $COP^2_{k,l}$ and $COP^2_{k,s}$ as a function of time.

The time evolution of $\Delta COP^2$ is represented in FIG. 5 for the illustrative test on one subject at normal gait on the force platform set-up. FIG. 5 presents the time evolution of $\Delta COP^2_{k,l}$ (curve C1 in solid line; left scale) and $\Delta COP^2_{k,s}$ (curve C2 in dashed line; right scale). The vertical dotted lines represent the separations between the single stances (S1, S2, S3) and double stances (D1, D2), detected on the basis of $\Delta COP^2_{k,l}$ and $\Delta COP^2_{k,s}$ peaks. The dashed horizontal line represents the $C_P$ threshold (equal to 0.0015 m² in this example), and the solid horizontal line represents the $C_F = C_L$ threshold (equal to 0.0003 m² in this example). This variable called $\Delta COP^2$ is the tool to determine the limits between the single and double stances before decomposing the GRF profiles, as described below.

Detection of Stance Transitions

The method to detect each transition between single and double stances consists of three consecutive steps:

Step 1: Detection of the $\Delta COP^2$ peak beginning in the next s samples, where s=fe/10=5:

$$\Delta COP^2_{k,s} > C_P \quad \text{Eq. 6}$$

Step 2: Detection of the exact first sample of the $\Delta COP^2$ peak:

$$\Delta COP^2_{k,l} > C_F \quad \text{Eq. 7}$$

Step 3: Detection of the exact last sample of the $\Delta COP^2$ peak:

$$\Delta COP^2_{k,l} < C_L \quad \text{Eq. 8}$$

where $C_P$ [m²] (P for peak), $C_F$ [m²] (F for first sample) and $C_L$ [m²] (L for last sample) are constant thresholds defined to distinguish the $\Delta COP^2$ peaks from the small variations of $\Delta COP^2$.

The rational for choosing the number s of samples in $\Delta COP^2 k,s$ is to have a compromise to ensure:

a sufficient number of samples to detect with certainty a $\Delta COP2$ peak that indicates a double stance phase (as presented in FIG. 5) and to detect this one early enough in the $\Delta COP2$ data to then search for the accurate peak start using $\Delta COP^2_{k,i}$; and a not too high number of samples, by remaining on the rising edge of the $\Delta COP2$ peak and not eventually after this one, to detect with certainty a $\Delta COP2$ peak that indicates a double stance phase.

For robustness, these thresholds are defined as $1 \times w^2 \times SF$, where:

1 is the number of samples corresponding to $\Delta COP^2_{k,i}$;

w [m] is the white noise magnitude measured in $\Delta COP^2_{k,l}$, approximately equal to 0.01 m in the present trials; and SF is a Security Factor in order to distinguish a peak of $\Delta COP^2_{k,l}$ from the measurement noise during the test, which is usually considered as Gaussian white noise. According to the definition of a Gaussian distribution, a variation of three standard deviations around its mean contains about 99.7% of the noise. Thus, the choice of SF equal to 3 enables to distinguish a peak signal from the noise measurement in 99.7% of cases. In 0.3% of the remaining cases where the peak has not been distinguished from the measurement noise, the peak will be identified at the next sample, following the present process.

Consequently, being given the white noise magnitude in the trials, CP (corresponding to $\Delta COP^2_{k,s}$ in Equation (6)) is here equal to $1 \cdot w2 \cdot SF = 5 \cdot 0.012 \cdot 3 = 0.0015$ m$^2$, and CF and CL (corresponding to $\Delta COP^2_{k,l}$ in Equations (7) and (8)) are here equal to $1 \cdot w2 \cdot SF = 1 \cdot 0.012 \cdot 3 = 0.0003$ m$^2$. On the basis of the detection of stance transitions (Equations (5) to (8)) and the above thresholds values, the detected separations between the single and double stances are illustrated in FIG. 5.

When the condition $\Delta COP^2_{k,s} > C_P$, it is determined that a peak will start within the next five sample points. Then, $\Delta COP^2_{k,l}$ is computed and compared to $C_F$. The first sample point for which $\Delta COP^2_{k,l} > C_F$ indicates the end of a single stance region and the beginning of a double stance region. Then, $\Delta COP^2_{k,l}$ is compared to $C_L$. the first sample point for which $\Delta COP^2_{k,l} < C_L$ indicates the end of the double stance region and the beginning of a further single stance region.

Decomposition of the GRFs

During each single foot stance time, the GRF resulting from the foot in contact with the platform set-up is equal to the total force, i.e. the measured global GRF, while the GRF under the foot in aerial phase is obviously equal to zero. During each double stance period, vertical GRF component under the foot that takes off from the platform set-up may be approximated by a cubic spline curve for example, noted $F_{z_{spline}}$. Vertical GRF component under the foot that lands on the platform set-up is approximated by $F_{z_{spline}} - F_{z_{tot}}$, where $F_{z_{tot}}$ is the global (summed) vertical GRF components measured on the platform set-up. Using splines has been chosen to approximate the GRF components under the foot that takes off from the platform set up, because their shapes during normal gait are generally smoother than the GRF components under the foot that lands on the platform set-up, the latter being reconstructed using the information contained in the globally measured vertical GRF. However, it should be understood that the GRF component under the foot that lands on the platform set-up may be first calculated using any adequate interpolation curve, and the GRF component under the foot that takes off from the platform set up may then be determined from the global GRF and the calculated GRF component under the foot that takes off.

Results

GRF Error Analysis

Figure 6:
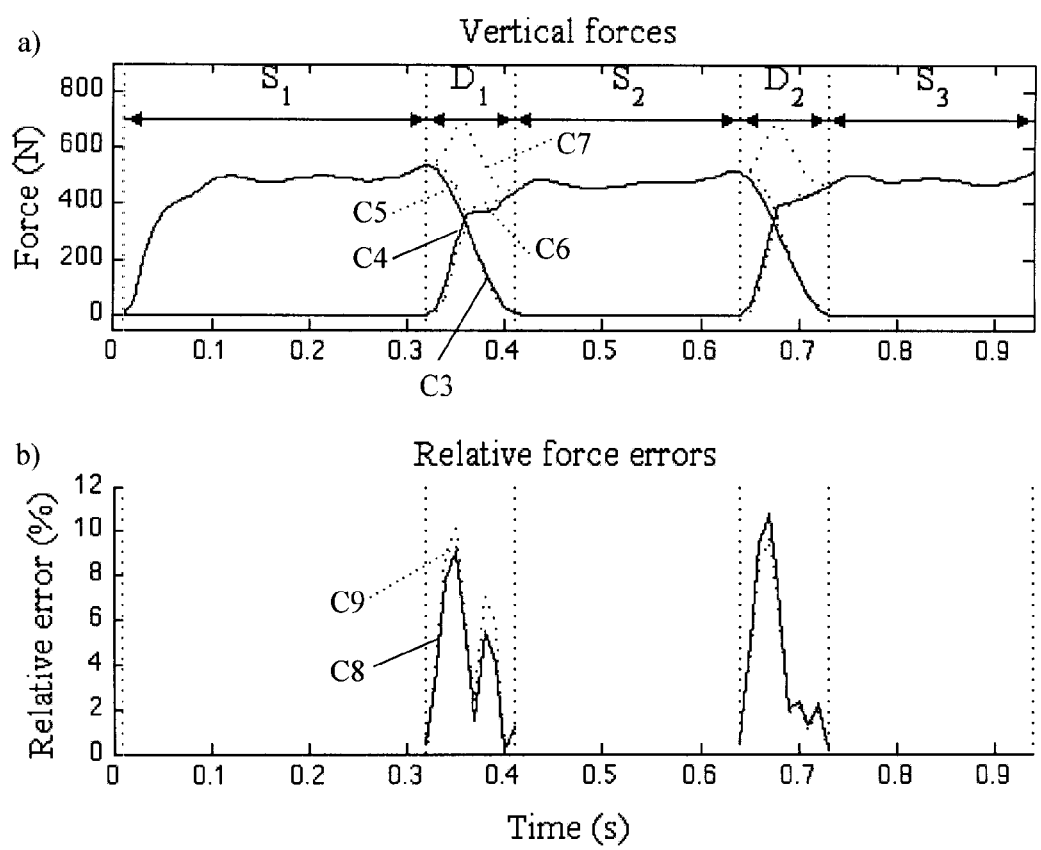
FIG. 6a is an exemplary graph of individual GRFs as a function of time obtained from the graph of FIG. 3.
FIG. 6b is a graph of a relative error percentage as a function of time.

Referring to the illustrative test shown in FIG. 5, the time evolution of the vertical component $F_z$ of the GRFs computed for each foot and the corresponding independently measured GRFs are presented in FIG. 6. FIG. 6a represents the time evolution of the vertical components of the GRFs approximated by splines (solid curves C3 and C4, for both support contacts) and the corresponding measured GRFs (dotted curves C5 and C6 for both support contacts). The total measured vertical GRFs are also presented (dotted curve C7) during the double stances detected by the $\Delta COP^2$ peaks. FIG. 6b represents the time evolution of the relative vertical GRF errors between the computed and measured GRFs, corresponding to the results in FIG. 6a, for the foot losing contact (solid curve C8) and the foot landing (dotted curve C9).

During the double stances, the absolute error is defined as:

$$e_{F_z} = \|F_{z_{computed}} - F_{z_{measured}}\| \qquad \text{Eq. 9}$$

where $F_{z_{measured}}$ is the measured vertical GRF and $F_{z_{computed}}$ is the computed vertical GRF during the double stance. Complementarily, we can define a relative error as follows:

$$\varepsilon_{F_z} = \frac{e_{F_z}}{\|F_{z_{max}}\|} \qquad \text{Eq. 10}$$

$$\varepsilon_{F_z} = \frac{e_{F_z}}{\|F_{z_{max}}\|}$$

where this relative error balances the impact of the absolute error $e_{F_z}$ relatively to the $F_{z_{max}}$, which is defined by the maximal total force during the double stance phase. This relative error is also presented in FIG. 6 during the double stances.

In order to summarize the statistical results of the 36 double stances, Table 1 successively presents the mean, root mean square (RMS) and maximum values of the relative and absolute errors between the computed and measured vertical GRFs. The mean and RMS errors also feature the standard deviation of these errors. Finally, Table 1 also presents the linear correlation coefficients $r_{\varepsilon_v}$ (resp. $r_{e_v}$) between these mean absolute (resp. relative) errors and the mean walking velocities.

TABLE 1

Statistical results of the 36 double stances: Mean $\epsilon_{mean}$ (resp. $e_{mean}$), rms $\epsilon_{rms}$ (resp. $e_{rms}$) and maximum $\epsilon_{max}$ (resp. $e_{max}$) values of the relative (resp. absolute) errors between the computed and measured GRFs. The mean and rms errors also feature the standard deviation of these errors. Linear correlation coefficients $r_{\varepsilon_v}$ (resp. $r_{e_v}$) between the mean relative (resp. absolute) errors and the mean gait velocities are also presented.

| $\epsilon_{mean}$ ± S.D (%) | $e_{mean}$ ± S.D (N) | $\epsilon_{rms}$ ± S.D (%) | $e_{rms}$ ± S.D (N) | $\epsilon_{max}$ (%) | $e_{max}$ (N) | $r_{\varepsilon_v}$ | $r_{e_v}$ |
|---|---|---|---|---|---|---|---|
| 3.8 ± 2.6 | 16.2 ± 8.4 | 5.7 ± 3.1 | 22.3 ± 10.1 | 24.1 | 68.0 | −0.15 | −0.02 |

Discussion And Conclusion

The main result reported in Table 1 is the low mean relative error of 5.0% between the vertical forces computed using the decomposition method, $F_{z_{computed}}$, and the corresponding measured vertical forces, $F_{z_{measured}}$, of 36 double stances of children (age: 9.3±2.9 years; weight: 35.1±11.1 kg) during untargeted gait on a unique force platform comprising seven force plates. This result represents the accuracy of the left-right vertical GRF components using the above-described decomposition method of forces, which is important to assess before using such results to analyze the GRF patterns or to compute the joint torques using either an inverse dynamic approach or the angular momentum, for example. No gait trial was rejected, in order to check the robustness of the present method. Based on 36 double stances, the algorithm robustness can be considered as reasonable regarding the standard deviation of the relative error (3.5%) in the decomposed forces, as given in Table 1. Finally, the linear correlation coefficients presented in Table 1, $r_{\varepsilon_v}$ equal to −0.16, and $r_{e_v}$ equal to −0.02, show that the relative and absolute errors of the force decomposition are not correlated with gait velocity.

In one embodiment, the above-described decomposition method is compared to a prior art method in which the limits of the single and double stances are determined by the side-to-side oscillations of the global COP and global GRFs. However these limits can hardly be identified accurately because medio-lateral position of the COP does not systematically show a clear side-to-side inflection point that can be determined by either a visual inspection or a systematic detection of the COP plot. Consequently, the prior art cannot be implemented in a systematic decomposition algorithm on a device, and is further not applicable for any gait pattern, even with a visual inspection. Finally, the assumption of the side-to-side inflection point may be particularly questionable in children gait analysis because of the GRF pattern variability and the resulting COP variability. In the above-described method, the limits of the single and double stances are determined by the peaks of a variable called $\Delta COP^2$ that is very sensitive to subject COP displacement during gait (e.g. in FIG. 5). Moreover, the condition applied on $\Delta COP^2$ in Equations (6) to (8) may be easily computed, and result in a systematic determination of the stance phases in typically developing children.

Secondly, the problem of force decomposition on a single platform consists in a system of two equations, the one describing the equilibrium of forces in the vertical direction, and the other one describing the equilibrium of moments about an anteroposterior axis of the force plate. In one embodiment, a first difference compared to the prior art method has been the measurement of these antero-posterior and medio-lateral forces and their use in the equilibrium equations. Further, these equations include four unknowns, both left and right vertical forces and both left and right positions of the COP on the lateral axis, leading to a problem of uncertainty. So, a second difference compared to the prior art method is the way in which this uncertainty is solved. After having supposed that a clear side-to-side inflection point can be detected, the prior art method arbitrarily fixes the medio-lateral COP coordinates of the foot that takes off from the platform set-up during the double stance to threshold constants, representing the minimum and maximum excursions of the measured COP. This leads to an absolute error of around 3 cm on the COP of the foot that takes off. This error has a clear impact on the accuracy of the decomposed GRFs, following the COP-GRF relation reminded by Equation (2). In the above-described method, the vertical GRF under the foot that takes off from the platform set-up during the double stance is approximated by cubic spline curves, $F_{z_{spline}}$, between its last value, equal to $F_{z_{tot}}$, at the transition from the single to the double stance, and its final value of zero, at the end of this double stance. During this double stance, the total vertical GRF of both feet, measured by $F_{z_{tot}}$, is respected because the GRF components under the foot that lands on the platform set-up are approximated by $F_{z_{tot}} - F_{z_{spline}}$, so that the sum of GRFs under the left and right feet is always equal to the measured global GRF. The rational for usage of a cubic spline interpolation to approximate the GRF components under the foot that takes off from the platform set up was justified by the fact that cubic spline curves are made to interpolate smooth transitions, enabling to take into account the fact that GRF shapes under the foot that takes off are smoother than GRF shapes under the foot that lands on the platform set-up, which show variable impacts at each step due to heel strike. In one embodiment, amongst interpolation techniques, cubic spline interpolation is generally preferred over polynomial interpolations because the interpolation error are smaller than low degree polynomial splines, and spline interpolation avoids the problem of Runge's phenomenon, i.e. oscillation at the edges of an interval, which occurs with high degree polynomials. However, it should be understood that any other adequate interpolation curve may be used, such as a linear spline curve, a square spline curve, a polynomial interpolation curve, or the like. Similarly, it should be understood that an adequate parametric curve may be used in replacement of an interpolation curve.

Thirdly, the above-described method was tested on 36 double stances (6 double stances×6 children) during untargeted gait. For these trials, the validation consisted in systematically comparing the vertical forces computed using the decomposition method, $F_{z_{computed}}$, and the corresponding actually measured vertical forces, $F_{z_{measured}}$. In an embodiment, the prior art method was only tested on one male adult subject (age: 32 years; weight: 700 N, i.e. around twice the mean value of the children weight here: 344.3 N), performing only two times three gait trials at different velocities. Further, the results of force decomposition were not presented considering the whole double stance, which does note enable one to assess the mean or maximal errors of the decomposed forces, and consequently does not enable one to appreciate the quality of the prior art method. Finally, in the prior art method test, there is no indication as to whether the subject performed untargeted gait on both Kistler force plates they used (model: 9287; length/width: 0.42 m).

In one embodiment, the above-described method focuses on the vertical component of ground reaction force (vGRF) because it represents the major component of the ground reaction force during gait, and the vertical ground reaction force is a useful information to characterize kinetic gait pattern. These vGRFs are commonly used as biomechanical indicators in gait evaluation, particularly in diabetic neuropathy, chronic stroke, scoliosis, or following hip arthoplasty. Besides gait evaluation, vGRFs are commonly used in analyzes of running, jumping, sit-to-stand and standing balance. Moreover, several walkway systems only measure the vertical component of the ground reaction force with large force plate.

In one embodiment, the detection of stance transitions depends on threshold values, which depend on the white noise magnitude, w. This one consists in the static white noise of the measurement system only, i.e. the plain system without including all dynamic components on the platform. Additional noise components introduced by the subject movement, such as the resonance of the platforms after a hard landing of a foot or after the lift off of a foot, or the force offset drifts during the measurement, could be accounted for by increasing SF. The robustness has only been calculated considering a subset of possible practical measurement side-effects/errors and only considering healthy children, which perform a more homogeneous movement pattern than disabled children.

In one embodiment, the above-described method for determining the GRF peaks using the mean and standard deviation of the global GRF may be adapted to determine the minimums of the global GRF. In this case, the first step consists in filtering the sample points and only keeping the sample points that meet the condition expressed by Equation (10):

$$\text{Global GRF} < \text{mean(global GRF)} - x.\text{SD(global GRF)} \quad \text{Eq. 10}$$

Then, the minimum points are determined considering only the sample points that meet the above condition. The time distances between two successive minimums may be determined, the average period of the global GRF signal may be obtained by averaging the determined time distances.

It should be understood that the above-described method for determining maximums or minimums of a global GRF signal using the mean and standard deviation may be used for determining the maximums, minimums, and/or period of any adequate biomechanical variable measured during the execution of a periodic or quasi-periodic movement by a subject.

In one embodiment, the above-described method is embodied as an apparatus comprising a processing unit operatively connected to a data storing unit storing executable instructions thereon that when executed by the processing unit perform the steps of the above-described method.

Figure 7:
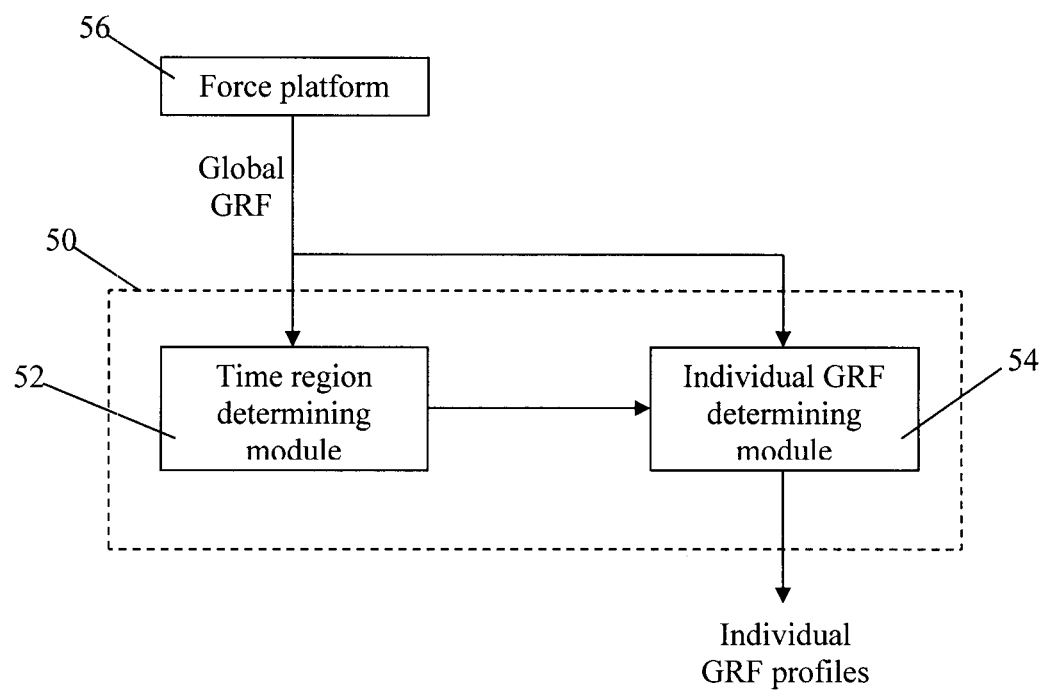
FIG. 7 is a block diagram illustrating of system for decomposing a global GRF into individual force profiles, in accordance with an embodiment.

FIG. 7 illustrates one embodiment of a system 50 for extracting individual GRFs from a global GRF. The system 50 comprises a time region determining module 52 and an individual GRF determining module 54.

The time region determining module 52 is adapted to receive the global GRF from the force platform, identify individual time regions within the global GRF using the above-described method, and assign a respective motion configuration to each time region using an identification of a reference motion configuration such as the first motion configuration and a logical order of motion configurations, as described-above with respect to methods 1, 10, and 30.

In one embodiment, the logical order of motion configurations is retrieved from a local memory. In another embodiment, the logical order is received as an input from a user computer for example.

In one embodiment, the identification of the reference motion configuration is retrieved from a local memory. In another embodiment, the identification of the reference motion configuration is received as an input from a user computer for example. In a further embodiment, the time region determining module 52 is further adapted to determine the reference motion configuration by determining the lateral displacement of the global center of pressure for example, as described above.

The time region determining module 52 is adapted to transmit the identification of the time regions and their respective motion configuration to the individual GRF determining module 54 along with the global GRF. The individual GRF determining module 54 is adapted to determine the individual GRF for each support contact using the received input and using the above-described method. For example, the individual GRF determining module 54 may use at least one interpolation function or at least one parametric function to determine the individual GRFs.

When applied to the walk of a person on a force platform 56, the time region determining module 52 is adapted to receive from the force platform 56 the global GRF that was measured while a subject moves thereon, and determine the single and double stance regions that are comprised in the received global GRF using any of the above-described method. The time region determining module 52 is further adapted to transmit an identification of the single and double stance regions to the individual GRF determining module 54. The identification may comprise a start time and an end time for each single stance region. In another example, the identification may comprise the start time and the end time for the double stance regions.

The individual GRF determining module 54 is adapted to receive the global GRF from the force platform or from the time region determining module 52 in addition to the identification of the single and double stance regions from the stance region determining module 52. The individual GRF determining module 54 is further adapted to determine the individual GRF profiles, i.e. the GRF caused by each foot of the subject, using the above-described method, and to output the individual GRF profiles.

In one embodiment, the time region determining module 52 is further adapted to determine the reference motion configuration as described above with respect to the method 20.

It should be understood that the modules 52 and 54 may be each provided with a processing unit configured to execute their respective method steps, a storing unit or memory, and communication means for receiving and/or transmitting data. Alternatively, the modules 52 and 54 may share a same processing unit, a same storing unit, and a same communication means.

In one embodiment, the force platform is multi-pedestal, i.e. it comprises a single plate on which the subject may place at least two steps. For example, the single force platform may be positioned under a treadmill belt. In another embodiment, the force platform comprises a plurality of plates positioned to form a single platform. In this case, the system further comprises a GRF combination unit adapted to add the global GRFs measured by the plurality of plates together. For example, the GRF combination unit receives the individual global GRFs, such as the individual global vertical GRFs, measured by the different plates and add them together to output a single value for the global GRF to be decomposed into individual force profiles.

It should be understood that the dimensions of the force platform are chosen so that the subject may perform at least one movement thereon such as at least one step.

The force platform is provided with an adequate number of force sensors for measuring a single component of the global GRF or the three-dimensional components of the global GRF for example. Examples of adequate force sensors comprise load cells, force transducers, strain gauges, piezoelectric sensors, capacitance gauges, piezoresistive sensors, and/or the like.

It should be understood that the above-described methods may be embodied as a device for decomposing a ground reaction force into individual force profiles, comprising a processing unit and a storing unit operatively coupled to the processing unit, the storing unit for storing executable instructions that, upon execution by the processing unit, perform the steps of the methods.

The embodiments of the invention described above are intended to be exemplary only. The scope of the invention is therefore intended to be limited solely by the scope of the appended claims.

I claim:

1. A computer-implemented method for decomposing a ground reaction force (GRF) into individual force profiles, comprising:
   receiving a time measurement of a global GRF measured while a subject having two support contacts for abutting a force platform performs at least one movement on the force platform, the movement comprising at least two motion configurations and each motion configuration being characterized by a respective number of said two support contacts being in physical contact with the force platform;
   identifying individual time regions contained in the time measurement of the global GRF and assigning a respective one of the at least two motion configurations to each time region using a logical order of motion configurations and an identification of a reference motion configuration, thereby identifying the motion configurations contained in the time measurement of the global GRF;

for each time region, determining an individual GRF for each one of the two support contacts using the identification of the motion configuration for the time region, the time measurement of the global GRF, and one of an interpolation function and a parametric equation, the one of an interpolation function and a parametric equation being used to model an individual GRF of a first one of the two support contacts that takes off from the force platform, an individual GRF of a second one of the two support contacts being determined using the global GRF and the individual GRF of the first one of the two support contacts, thereby determining a contribution of each one of the at least two support contacts to the global GRF; and outputting the individual GRFs;

said identifying individual time regions comprising determining single stance regions and double stance regions within the global GRF;

said assigning comprising:

assigning a first one of the two support contacts considered as being in contact with the force platform to a first single stance region and assigning the first one of the two support contacts to each subsequent odd single stance region;

assigning a second one of the two support contacts considered as being in contact with the force platform to the second single stance region, the first one of the two support contacts being considered to be away from the force platform, and assigning the second one of the two support contacts to each subsequent even single stance region; and said determining an individual GRF comprising:

for each odd single stance region, assigning a corresponding value of the global GRF to a force of the first one of the two support contacts and a substantially zero value to a force of the second one of the two support contacts;

for each even single stance region, assigning a corresponding value of the global GRF to the force of the second one of the two support contacts and the substantially zero value to the force of the first one of the two support contacts; and for each double stance value, determining a first value for the force of the first one of the two support contacts and a second value for the force of the second one of the two support contacts, the sum of the first and second values being equal to the value of the global, thereby obtaining individual support force profiles.

2. The computer-implemented method of claim 1, wherein the logical order of motion configuration comprises a sequence of motion configurations to be executed by the subject on the force platform.

3. The computer-implemented method of claim 2, wherein the logical order of motion configuration further comprises an identification of the support contacts that are in physical contact with the force platform for each motion configurations contained in the logical order.

4. The computer-implemented method of claim 1, wherein the reference motion configuration comprises one of a first motion configuration and a last motion configuration.

5. The computer-implemented method of claim 1, wherein said determining the single and double stance regions comprises:

determining a squared Euclidian norm $\Delta COP^2_{k,l}$ between two sample points k and l using the global GRF;

comparing $\Delta COP^2_{k,l}$ to a first threshold;

determining a beginning of a double stance region when $\Delta COP^2_{k,l}$ is greater than the first threshold;

comparing $\Delta COP^2_{k,l}$ to a second threshold; and determining a beginning of a single stance region when $\Delta COP^2_{k,l}$ is less than the second threshold.

6. The computer-implemented method of claim 5, further comprising:

determining a squared Euclidian norm $\Delta COP^2_{k,s}$ between the sample points k and a predetermined number s of measurement points using the global GRF, s being greater than one;

comparing $\Delta COP^2_{k,s}$ to a third threshold; and predicting that a squared Euclidian norm peak will occur within the predetermined number s of measurement points.

7. The computer-implemented method of claim 1, wherein said determining the single and double stance regions comprises:

determining the peak points in time at which a GRF peak occurs;

determining a squared Euclidian norm $\Delta COP^2_{k,l}$ between two sample points k and l using the global GRF; and starting from each peak point in time, determining a first last point in time for which $\Delta COP^2_{k,l}$ is greater than a first threshold, the first last point in time separating a first single stance region from a given double stance region, and determining a second last point in time for which $\Delta COP^2_{k,l}$ is less than a second threshold, the second last point in time separating the given double stance region from a second single stance region.

8. The computer-implemented method of claim 1, further comprising determining the identification of the reference motion configuration using a lateral displacement in time of a global center of pressure.

9. A system for decomposing a ground reaction force (GRF) into individual force profiles, comprising:

a stance region determining module for:

receiving a time measurement of a global GRF measured while a subject having two support contacts for abutting a force platform performs at least one movement on the force platform, the movement comprising at least two motion configurations and each motion configuration being characterized by a respective number of said two support contacts being in physical contact with the force platform;

identifying individual time regions contained in the time measurement of the global GRF and assigning a respective one of the at least two motion configurations to each time region using a logical order of motion configurations and an identification of a reference motion configuration, thereby identifying the motion configurations contained in the time measurement of the global GRF; and an individual GRF determining module for:

for each time region, determining an individual GRF for each one of the two support contacts using the identification of the motion configuration for the time region, the time measurement of the global GRF, and one of an interpolation function and a parametric equation, the one of an interpolation function and a parametric equation being used to model an individual GRF of a first one of the two support contacts that takes off from the force platform, an individual GRF of a second one of the two support contacts being determined using the global GRF and the individual GRF of the first one of the two support contacts, thereby determining a contribution of each one of the at least two support contacts to the global GRF; and outputting the individual GRFs;

the stance region determining module being adapted to:
    determine single stance regions and double stance regions within the global GRF;
    assign a first one of the two support contacts considered as being in contact with the force platform to a first single stance region and assigning the first one of the two support contacts to each subsequent odd single stance region;
    assign a second one of the two support contacts considered as being in contact with the force platform to the second single stance region, the first one of the two support contacts being considered to be away from the force platform, and assigning the second one of the two support contacts to each subsequent even single stance region; and the individual GRF determining module is adapted to:
    for each odd single stance region, assign a corresponding value of the global GRF to a force of the first one of the two support contacts and a substantially zero value to a force of the second one of the two support contacts;
    for each even single stance region, assign a corresponding value of the global GRF to the force of the second one of the two support contacts and the substantially zero value to the force of the first one of the two support contacts; and
    for each double stance value, determine a first value for the force of the first one of the two support contacts and a second value for the force of the second one of the two support contacts, the sum of the first and second values being equal to the value of the global, thereby obtaining individual support contact force profiles.

10. The system of claim 9, wherein the logical order of motion configuration comprises a sequence of motion configurations to be executed by the subject on the force platform.

11. The system of claim 10, wherein the logical order of motion configuration further comprises an identification of the support contacts that are in physical contact with the force platform for each motion configurations contained in the logical order.

12. The system of claim 9, wherein the reference motion configuration comprises one of a first motion configuration and a last motion configuration.

13. The system of claim 9, wherein the stance region determining module is adapted to:
    determine a squared Euclidian norm $\Delta COP^2_{k,l}$ between two sample points k and l using the global GRF;
    compare $\Delta COP^2_{k,l}$ to a first threshold;
    determine a beginning of a double stance region when $\Delta COP^2_{k,l}$ is greater than the first threshold;
    compare $\Delta COP^2_{k,l}$ to a second threshold; and
    determine a beginning of a single stance region when $\Delta COP^2_{k,l}$ is less than the second threshold.

14. The system of claim 13, wherein the stance region determining module is further adapted to:
    determine a squared Euclidian norm $\Delta COP^2_{k,s}$ between the sample points k and a predetermined number s of measurement points using the global GRF, s being greater than one;
    compare $\Delta COP^2_{k,s}$ to a third threshold; and
    predict that a squared Euclidian norm peak will occur within the predetermined number s of measurement points.

15. The system of claim 9, wherein the stance region determining module is further adapted to:
    determine the peak points in time at which a GRF peak occurs;
    determine a squared Euclidian norm $\Delta COP^2_{k,l}$ between two sample points k and l using the global GRF; and
    starting from each peak point in time, determine a first last point in time for which $\Delta COP^2_{k,l}$ is greater than a first threshold, the first last point in time separating a first single stance region from a given double stance region, and determine a second last point in time for which $\Delta COP^2_{k,l}$ is less than a second threshold, the second last point in time separating the given double stance region from a second single stance region.

16. The system of claim 9, wherein the stance region determining module is further adapted to determine the identification of the reference motion configuration using a lateral displacement in time of a global center of pressure.

17. A computer-implemented method for decomposing a ground reaction force (GRF) into individual force profiles, comprising:
    receiving a time measurement of a global GRF measured while a subject having two support contacts for abutting a force platform performs at least one movement on the force platform, the movement comprising at least two motion configurations and each one of the at least two motion configurations corresponding to one of a single stance configuration and a double stance configuration;
    identifying individual time regions contained in the time measurement of the global GRF and assigning a respective one of the at least two motion configurations to each time region using a logical order of motion configurations and an identification of a reference motion configuration, thereby identifying the motion configurations contained in the time measurement of the global GRF, said assigning comprising:
        assigning a first one of the two support contacts considered as being in contact with the force platform to a first single stance region and assigning the first one of the two support contacts to each subsequent odd single stance region;
        assigning a second one of the two support contacts considered as being in contact with the force platform to the second single stance region, the first one of the two support contacts being considered to be away from the force platform, and assigning the second one of the two support contacts to each subsequent even single stance region; and
    for each time region, determining an individual GRF for each one of the two support contacts using the identification of the motion configuration for the time region and the time measurement of the global GRF, thereby determining a contribution of each one of the at least two support contacts to the global GRF, said determining an individual GRF comprising:
        for each odd single stance region, assigning a corresponding value of the global GRF to a force of the first one of the two support contacts and a substantially zero value to a force of the second one of the two support contacts;

for each even single stance region, assigning a corresponding value of the global GRF to the force of the second one of the two support contacts and the substantially zero value to the force of the first one of the two support contacts; and for each double stance value, determining a first value for the force of the first one of the two support contacts and a second value for the force of the second one of the two support contacts, the sum of the first and second values being equal to the value of the global, thereby obtaining individual support contact force profiles; and outputting the individual GRFs, wherein said determining the single and double stance regions comprises:

determining a squared Euclidian norm $\Delta COP^2_{k,l}$ between two sample points k and l using the global GRF;

comparing $\Delta COP^2_{k,l}$ to a first threshold;

determining a beginning of a double stance region when $\Delta COP^2_{k,l}$ is greater than the first threshold;

comparing $\Delta COP^2_{k,l}$ to a second threshold; and determining a beginning of a single stance region when $\Delta COP^2_{k,l}$ is less than the second threshold.

* * * * *